(12) United States Patent
Puchades et al.

(10) Patent No.: US 8,751,172 B2
(45) Date of Patent: Jun. 10, 2014

(54) MICROELECTROMECHANICAL VISCOSITY MEASUREMENT DEVICES AND METHODS THEREOF

(75) Inventors: Ivan Puchades, West Henrietta, NY (US); Lynn Fuller, Canandaigua, NY (US)

(73) Assignee: Rochester Institute of Technology, Rochester, NY (US)

( * ) Notice: Subject to any disclaimer, the term of this patent is extended or adjusted under 35 U.S.C. 154(b) by 177 days.

(21) Appl. No.: 12/826,156

(22) Filed: Jun. 29, 2010

(65) Prior Publication Data

US 2010/0332155 A1    Dec. 30, 2010

Related U.S. Application Data

(60) Provisional application No. 61/221,332, filed on Jun. 29, 2009.

(51) Int. Cl.
  *G01N 11/00* (2006.01)
  *H01L 21/70* (2006.01)
(52) U.S. Cl.
  USPC ............ 702/50; 73/54.01; 73/54.38; 73/861; 73/53.01; 73/204.11; 73/54.42
(58) Field of Classification Search
  USPC .......... 702/50; 73/54.01, 54.23, 54.25, 54.26, 73/54.27, 54.32, 54.38, 54.41, 32 A, 24.05, 73/54.17, 23.2, 861, 53.01, 204.11, 54.42; 378/147, 149, 155; 250/505.1
  See application file for complete search history.

(56) References Cited

U.S. PATENT DOCUMENTS

| | | | | |
|---|---|---|---|---|
| 4,023,562 A | * | 5/1977 | Hynecek et al. | 600/561 |
| 4,926,682 A | * | 5/1990 | Holm-Kennedy et al. | 73/54.01 |
| 6,269,685 B1 | * | 8/2001 | Oden | 73/54.23 |
| 6,311,549 B1 | * | 11/2001 | Thundat et al. | 73/54.24 |
| 6,457,360 B1 | | 10/2002 | Daraktchiev et al. | |
| 6,495,388 B1 | * | 12/2002 | Ismail | 438/53 |
| 6,668,621 B1 | * | 12/2003 | Wright | 73/54.25 |
| 7,284,413 B2 | * | 10/2007 | Ehwald et al. | 73/54.23 |
| 7,763,487 B2 | * | 7/2010 | Villa et al. | 438/50 |
| 7,775,084 B2 | * | 8/2010 | Huq et al. | 73/54.27 |
| 7,785,098 B1 | * | 8/2010 | Appleby et al. | 425/470 |
| 7,811,848 B2 | * | 10/2010 | Barlocchi et al. | 438/52 |
| 7,874,199 B2 | * | 1/2011 | Chaudoreille et al. | 73/32 A |

(Continued)

FOREIGN PATENT DOCUMENTS

| | | |
|---|---|---|
| WO | 2005/054817 A1 | 6/2005 |
| WO | 2007/104978 A1 | 9/2007 |
| WO | 2009/022121 A2 | 2/2009 |

OTHER PUBLICATIONS

Arya et al., "Thermally Actuated, Bistable, Oxide/Silicon/Metal Membranes," J. Micromech. Microeng. 16:40-7 (2006).

(Continued)

*Primary Examiner* — Carol S Tsai
(74) *Attorney, Agent, or Firm* — Joseph M. Noto; Bond Schoeneck & King PLLC (57) ABSTRACT

A viscosity measurement device includes a flexible membrane, an actuation heating element, and a displacement sensor apparatus. The actuation heating element is on and spaced in from an outer periphery of the flexible membrane. The displacement sensor apparatus is coupled to the flexible membrane and measures and outputs a displacement signal representative of a viscosity of a fluid in contact with the flexible membrane.

32 Claims, 10 Drawing Sheets

(56) References Cited

U.S. PATENT DOCUMENTS

| | | | |
|---|---|---|---|
| 8,049,193 B1* | 11/2011 | Appleby et al. | 250/505.1 |
| 2003/0230136 A1 | 12/2003 | Wright | |
| 2004/0223884 A1* | 11/2004 | Chen et al. | 422/88 |
| 2006/0260408 A1* | 11/2006 | Villa et al. | 73/715 |
| 2008/0028837 A1* | 2/2008 | Djakov et al. | 73/54.38 |
| 2009/0084167 A1* | 4/2009 | Djakov et al. | 73/54.38 |
| 2011/0248211 A1* | 10/2011 | Matsumoto et al. | 252/78.3 |
| 2011/0302996 A1* | 12/2011 | Djakov et al. | 73/54.01 |
| 2012/0155242 A1* | 6/2012 | Duerig et al. | 369/154 |

OTHER PUBLICATIONS

Ayela et al., "Micromachined Piezoelectric Membranes with High Nominal Quality Factors in Newtonian Liquid Media: A Lamb's Model Validation at the Microscale," Author Manuscript 28 pages (2006).

Belmiloud et al., "Vibrating Microcantilever Used as Viscometer and Microrheometer," IEEE Sensors EXCO Daegu, Korea pp. 753-756 (2006).

Boley et al., Theory of Thermal Stress, John Wiley and Sons, Inc., pp. 379-409 (1985).

Chon et al., "Experimental Validation of Theoretical Models for the Frequency Response of Atomic Force Microscope Cantilever Beams Immersed in Fluids," Journal of Applied Physics 87(8):3978-88 (2000) (Abstract).

Dunn et al., "Deformation and Structural Stability of Layered Plate Microstructures Subjected to Thermal Loading," Journal of Microelectromechanical Systems 11(4):372-84 (2002) (Abstract).

Harrison et al., "A Microfluidic MEMS Sensor for the Measurement of Density and Viscosity at High Pressure," Proc. of SPIE 6465:64650U-1-64650U-13 (2007).

Huniti et al., "Behavior of Thermal Stresses in a Rapidly Heated Thin Plate," Journal of Thermal Stresses 23:293-307 (2000).

Kern et al., "Eine Einfache Versuchsanordnung Zur Universellen Prufung des Kelbeverbundes Im Axialen Zugtest," Dtsch Zahnarztl Z 48:769-772 (1993).

Kozlovsky, "Vibration of Plates in Contact with Viscous Fluid: Extension of Lamb's Model," Journal of Sound and Vibration 326:332-9 (2009).

Manrique De Lara et al., "Theoretical Model on the Interaction of a Vibrating Beam and the Surrounding Viscous Fluid with Applications to Density and Viscosity Sensors," IEEE, Schlumberger Cambridge Research, Cambridge, U.K. pp. 828-831 (2004).

Pionke et al., "The Various Approximations fo the Bimetallic Thermostatic Strip," Journal of Applied Mechanics 58:1015-20 (1991).

Puchades et al., "Design and Evaluation of a MEMS Bimetallic Thermal Actuator for Viscosity Measurements," Dept. of Microelectron. Eng., Rochester Inst. of Technol., Rochester, NY pp. 93-97 (2008).

Puers et al., "On the Mechanisms in Thermally Actuated Composite Diaphragms," Sensors and Actuators A 67:13-7 (1998).

Ramkumar et al, "P1I-7 Silicon Ultrasonic Horn Driven Microprobe Viscometer," IEEE, SonicMEMS Lab., Cornell Univ., Ithaca, NY pp. 1449-1452 (2006) (Abstract).

Sader, "Frequency Response of Cantilever Beams Immersed in Viscous Fluids with Applications to the Atomic Force Microscope," Journal of Applied Physics 84(1):64-76 (1998).

Young, Roark'S Formulas for Stress and Strain, McGraw-Hill Publishing Company, Sixth Edition, pp. 391-486 (1989).

Zou et al., "A Study on Micromachined Bimetallic Actuation," Sensors and Actuators 78:212-9 (1999).

* cited by examiner

TABLE I. TEMPERATURE INCREASE WITH A BIAS OF 0.5 WATTS ACCORDING TO EQUATIONS (13) AND (14) AND DIMENSIONS OF FIGURE 2.

| t | Rth | $\Delta T$ (0.5 W) |
|---|---|---|
| 10 μm | 278 °K/W | 34.7 °K |
| 20 μm | 139 °K/W | 17.3 °K |
| 30 μm | 93 °K/W | 11.5 °K |

*FIG. 10A*

TABLE II. PREDICTED VERTICAL MOVEMENT WITH TEMPERATURES OF TABLE 1 AND EQUATIONS (10), (11), AND (12).

| | BIMETAL AREA | | |
|---|---|---|---|
| t | 0% | 5% | 25% |
| 10 μm | 2.7 μm | 15 μm | 29 μm |
| 20 μm | 1.4 μm | 2.2 μm | 4 μm |
| 30 μm | 1 μm | 0.67 μm | 1.2 μm |

*FIG. 10B*

TABLE III. COMPARISON OF ANALYTICAL PREDICTION AND EXPERIMENTAL DEFLECTION DATA FOR 0.5 W BIAS.

| | BIMETAL AREA | | | | | |
|---|---|---|---|---|---|---|
| | 0% | | 5% | | 25% | |
| t | THEORY | EXP | THEORY | EXP | THEORY | EXP |
| 10 μm | 2.7 μm | 12 μm | 15 μm | 18 μm | 29 μm | <20 μm |
| 20 μm | 1.4 μm | 5 μm | 2.2 μm | 3 μm | 4 μm | 8 μm |
| 30 μm | 1 μm | 1 μm | 0.67 μm | 1 μm | 1.2 μm | <1 μm |

*FIG. 10C*

MICROELECTROMECHANICAL VISCOSITY MEASUREMENT DEVICES AND METHODS THEREOF

This application claims the benefit of U.S. Provisional Patent Application Ser. No. 61/221,332, filed Jun. 29, 2009, which is hereby incorporated by reference in its entirety.

FIELD

This technology generally relates to methods and devices for measuring viscosity and, more particularly, to microelectromechanical (MEMS) viscosity measurement devices and methods thereof.

BACKGROUND

Viscosity measurements are carried out with complex machines that required constant calibration and long wait times. Changes in oil viscosity in vehicles operated in extreme conditions result in major breakdowns and repairs. Preventive maintenance schedules may not be enough to prevent these breakdowns. As such in-field viscosity monitoring is needed.

Current MEMS based viscosity sensors utilize changes in resonant frequencies of cantilever beams to correlate viscosity changes. These devices are considered vibration viscometers in which the damping of an oscillating electromechanical resonator immersed in the test liquid is measured. Complex actuation and sensing methods, which are usually non-CMOS compatible, make these devices quite challenging to fabricate and integrate.

Some of these prior complex actuation and sensing devices utilize an electromagnetic driven cantilever beam or plate which requires the use of a strong external magnet and an optical readout method which is not easily integrated. Others prior devices use ultrasonic piezoelectric actuation of a very long microprobe which raises material reliability questions. The use of a piezoelectric membrane with an optical read which improves the reliability, although not the CMOS compatibility also has been suggested.

SUMMARY

A viscosity measurement apparatus includes a flexible membrane, an actuation heating element, and a displacement sensor apparatus. The actuation heating element is on and spaced in from an outer periphery of the flexible membrane. The displacement sensor apparatus is coupled to the flexible membrane and measures and outputs a displacement signal representative of a viscosity of a fluid in contact with the flexible membrane.

A method of making a viscosity measurement device includes providing an actuation heating element on and spaced in from an outer periphery of the flexible membrane. A displacement sensor apparatus is coupled to the flexible membrane and measures and outputs a displacement signal representative of a viscosity of a fluid in contact with the flexible membrane This technology provides a number of advantages including providing devices and methods for inexpensive, reliable, real time measurement of viscosity. Additionally, this technology is compatible with current CMOS fabrication. Further, the use of a membrane with this technology, as opposed to a cantilever beam, results in improved reliability and greatly simplified fabrication. Even further, this technology provides an output signal for the viscosity reading that is compatible with current electronics and is easily integrated.

DETAILED DESCRIPTION

Figure 1:
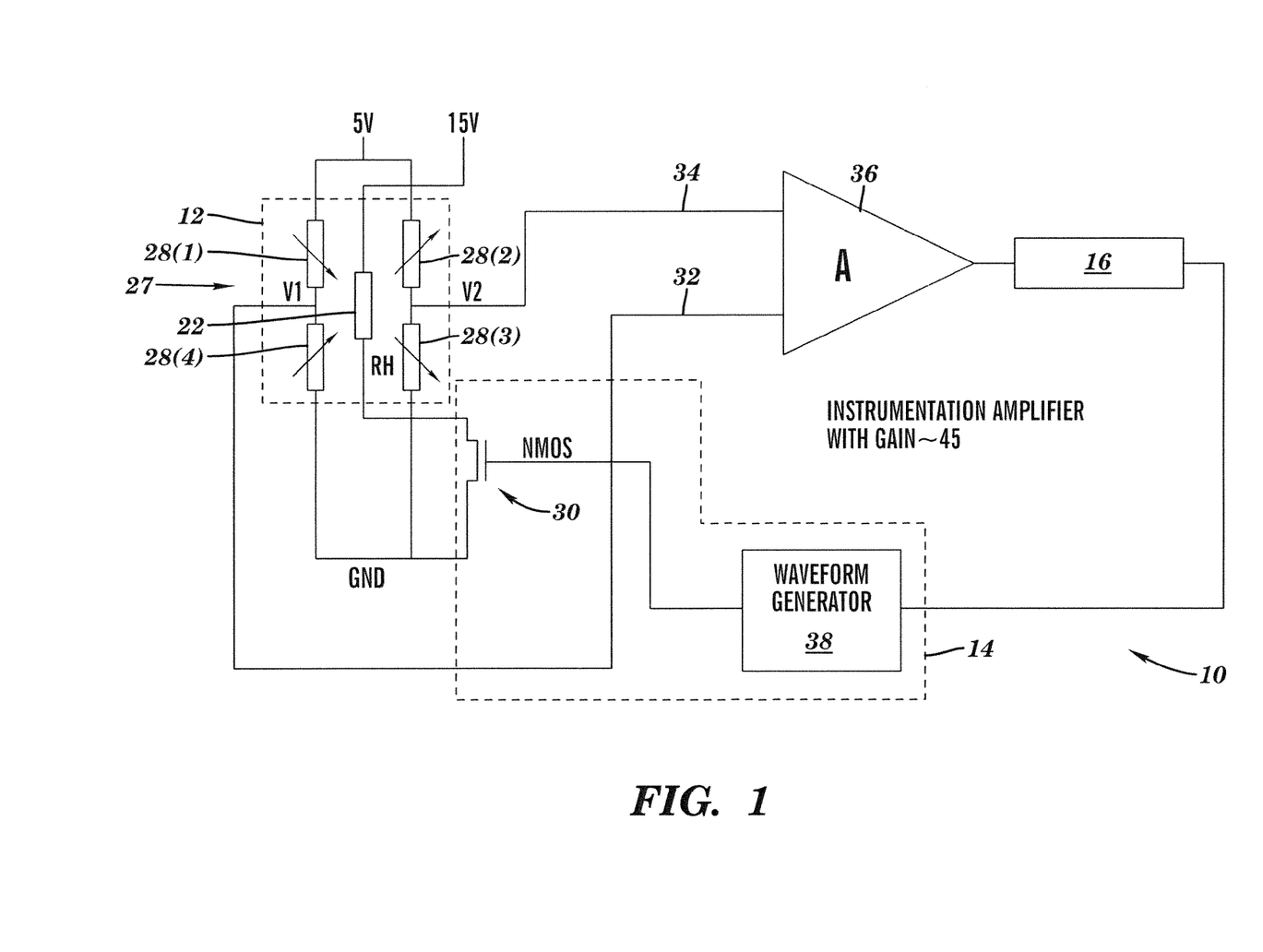
FIG. 1 is a block diagram of an exemplary viscometer system.
Figure 2:
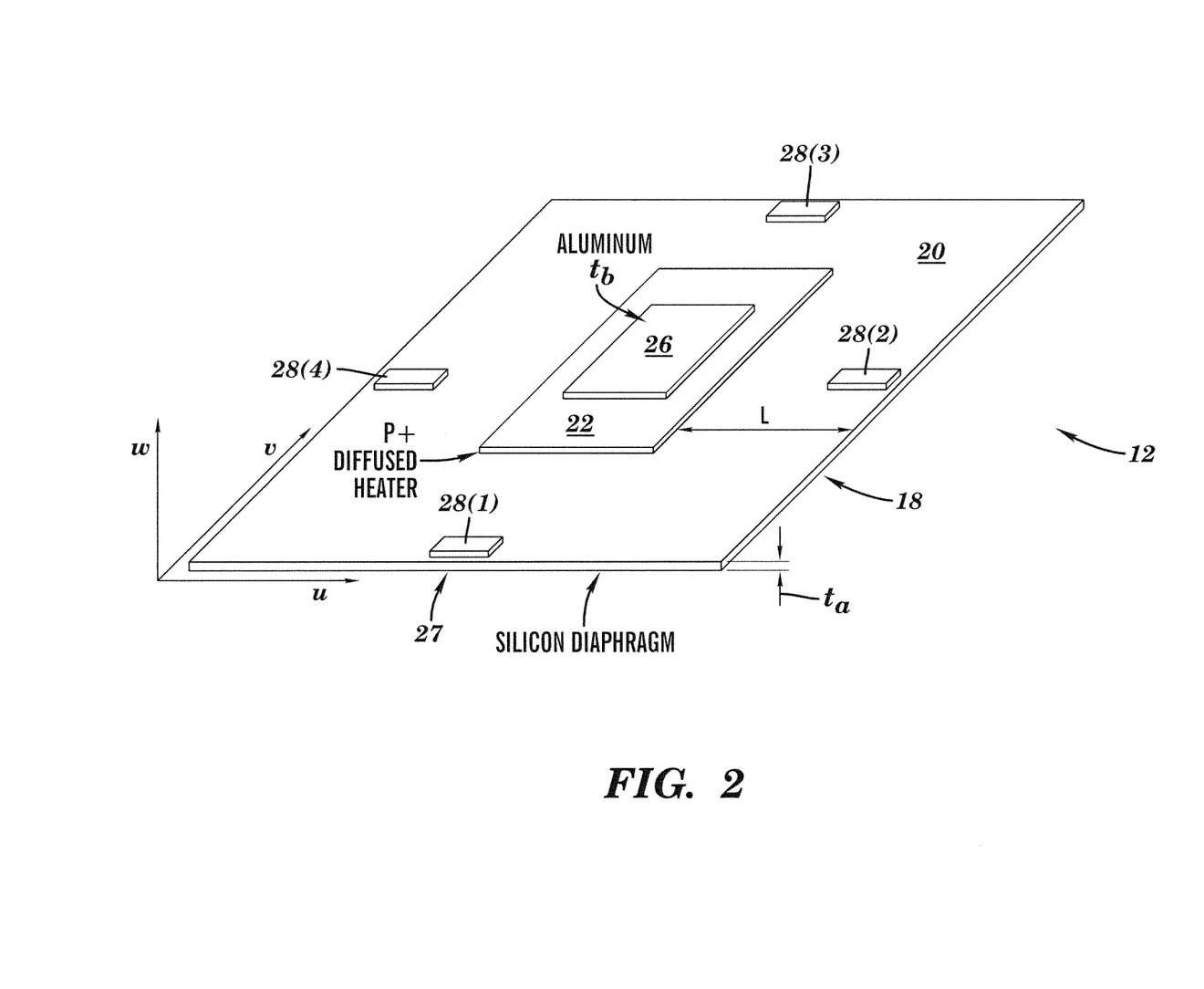
FIG. 2 is a top view of the viscosity measurement device in the exemplary viscometer system shown in FIG. 1.
Figure 3:
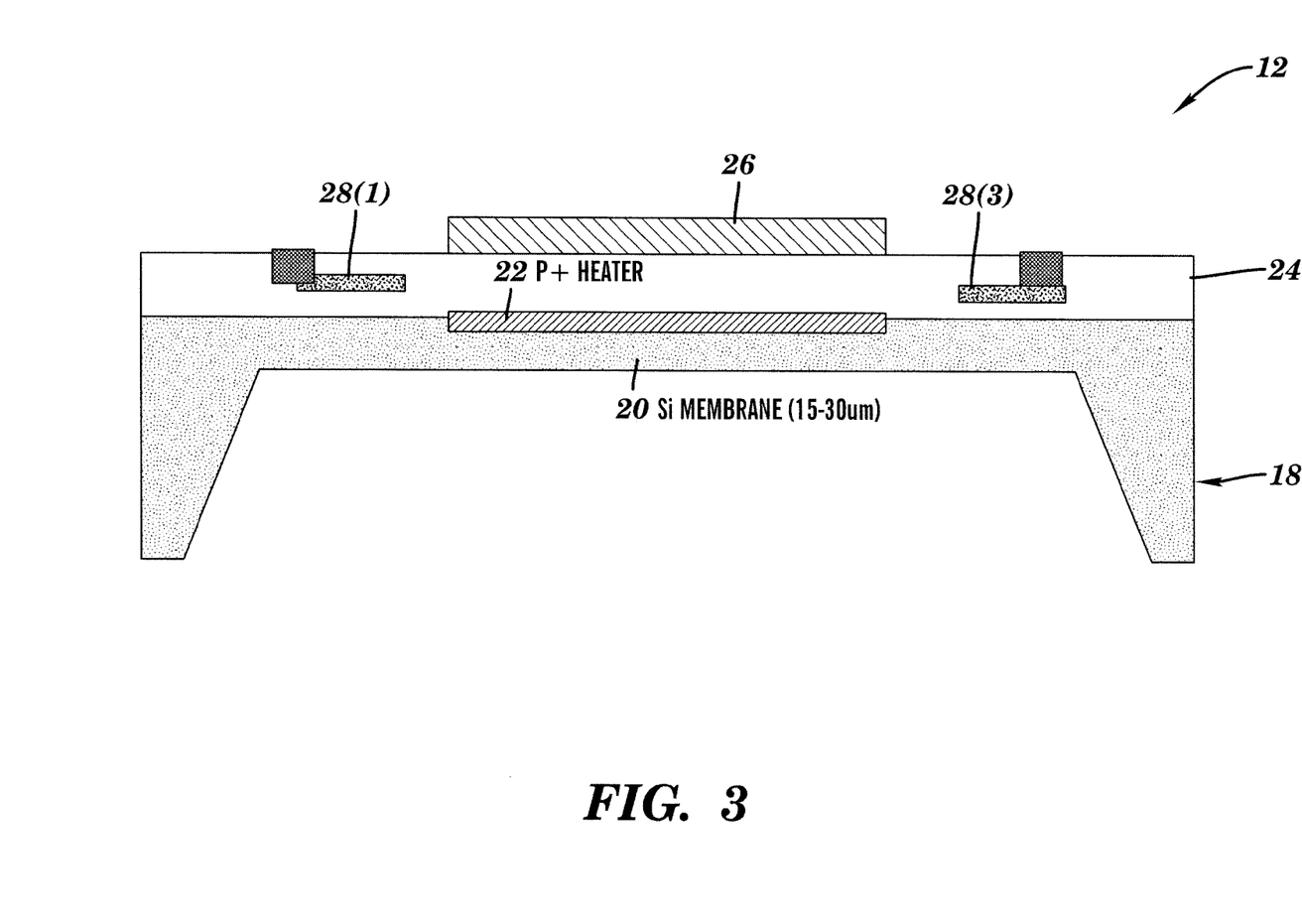
FIG. 3 is a side, cross-sectional view of the exemplary viscosity measurement device shown in FIGS. 1 and 2.

An exemplary viscometer system 10 is illustrated in FIGS. 1-3. The exemplary viscometer system 10 includes a viscosity measurement device 12, a driving device 14, and a viscosity computing device 16, although other types and numbers of systems, devices, components and other elements in other configurations could be used. This technology provides a number of advantages including providing devices and methods for inexpensive, reliable, real time measurement of viscosity.

Referring more specifically to FIG. 1, the viscosity measurement device 12 includes a supporting structure or substrate 18 with a membrane or other diaphragm region 20, a heating element 22, a thermal isolation layer 24, a metal plate 26, and a displacement sensor apparatus 27 comprising piezoresistive elements 28(1)-28(4) which are configured as a piezoresistive Wheatstone bridge, although other types and numbers of systems, devices, components and other elements in other configurations could be used.

The supporting structure or substrate 18 supports and fixes the outer edges or periphery of the membrane 20 which is flexible or moveable and is used to measure viscosity, although other types of supporting structures and moveable membranes in other configurations could be used. In this exemplary embodiment, the supporting structure or substrate 18 and the membrane 20 are formed from the same silicon material with the membrane 20 spaced in from and thinner than the outer edges or periphery of the supporting structure 18 as illustrated in FIG. 3, although other configurations with other types and numbers of elements and components, such as a separate supporting structure with a center opening with a separate flexible membrane fixed about its edges over the center opening of the supporting structure, could be used.

Although in this example the supporting structure 18 and the membrane 20 are made of silicon, other types and numbers of materials could be used.

The heating element 22 when engaged provides the necessary heat to create thermal expansion differences between the membrane 20 and the metal 20 plate 26 to result in a displacement of this resulting structure in the viscosity measurement device 12. In this example, the heating element 22 comprises a P+ doped region which is formed in and spaced in from all sides of the outer periphery of the membrane 20, although other types of actuation heaters which are made of other materials and in other manners could be used. Additionally, the 25 heating element 22 is coupled at one end to a fifteen volt power source and at the other end to the source of an NMOS field effect transistor 30 in the driving device 14, although the heating element can be coupled in other manners to other types of power sources for controlled engagement.

The thermal isolation layer 24 is formed over the heating element 22 and the membrane 20, although other types and numbers of layers in other configurations could be used. The thermal isolation layer 24 prevents the media whose viscosity is being measured by the viscosity measurement device 12 from being affected by the heating element 22.

The metal plate 26 is formed on the thermal isolation layer 24 and over or otherwise in at least partial alignment with the heating element 22 and is spaced in on all sides from the outer edges or periphery of the membrane 20, although other types and numbers of plates or other layers in other configurations could be used. In this example, the metal plate 26 comprises a layer of aluminum, although other types of materials could be used for the metal plate 26, such as tungsten or platinum by way of example only. A large difference of thermal expansion coefficient between the plate 26 and the membrane 20 on the order of at least twenty is desirable for these examples as discussed in greater detail herein. In the illustrated examples shown in FIGS. 1-3, the membrane 20 is made of silicon with a coefficient of thermal expansion of 2.3 ppm/C and the metal plate 26 is made of aluminum with a coefficient of thermal expansion of 22 ppm/C, although other materials with other thermal coefficients could be used.

The displacement sensor apparatus 27 comprising the piezoresistive elements 28(1)-28(4) change in resistance in response to displacement and this change in resistance is used to measure and output the displacement of the membrane 20 in a media whose viscosity is being analyzed, although other types and numbers of sensing elements and device in other configurations could be used. In this example, the piezoresistive elements 28(1)-28(4) with conductive contacts at opposing ends are formed in the thermal isolation layer 24 and are positioned about and spaced from the heating element 22 adjacent an outer perimeter of the membrane 20, although other types and numbers of sensing elements in other configurations could be used. The piezoresistive elements 28(1)-28(4) are coupled to form a piezoresistive Wheatstone bridge, which is used to measure the displacement of the membrane 20 and metal plate 26, although other types of sensing devices for determining displacement could be used. In this example, one end of the piezoresistive elements 28(1) and 28(2) are each coupled to a 5 volt power source, one end of piezoresistive elements 28(3) and 28(4) are each coupled to ground, and the other ends of piezoresistive elements 28(1) and 28(2) are each coupled in series to the other ends of piezoresistive elements 28(4) and 28(3), respectively, although other configurations could be used. One input 32 to an differential amplifier 36 is coupled between the piezoresistive elements 28(1) and 28(4) and another input 34 to the differential amplifier 32 is coupled between the piezoresistive elements 28(2) and 28(3), to provide an output signal to the viscosity computing device 16 representative of the measured displacement of the membrane 20, although the signal could be output to other types of devices, such as an oscilloscope or other display device or to a storage device by way of example only. Accordingly, as illustrated in the examples above the viscosity measurement device 12 can be built using standard microelectronic fabrication and is CMOS compatible.

The driving device 14 is used to selectively control the application of power to the heating element 22 to induce vibrations in the membrane 20, although other manners for controlling the viscosity measurement device 12 could be used. In this example, the driving device 14 comprises a waveform generator 38 whose output is coupled to a gate of the NMOS field effect transistor 30, although other types and numbers of components and other elements in other configurations could be used. The source of the NMOS field effect transistor 30 is coupled to the other end of the heating element 22 and the drain of the NMOS field effect transistor 30 is coupled to ground, although other configurations could be used.

The viscosity computing device 16 is coupled to the output of the amplifier 36 and receives an output signal representative of the displacement of the membrane 20 and metal plate 26, although other types and numbers of devices could receive the output signal, such as an oscilloscope or other display device or a storage device for recording the captured displacement for later processing. The viscosity computing device 16 includes a central processing unit (CPU) or processor, a memory, and an interface or I/O system, which are coupled together by a bus or other link, although other numbers and types of processing devices could be used. The processor in the viscosity computing device 16 executes a program of stored instructions for one or more aspects of the technology as described and illustrated herein. The memory 22 stores these programmed instructions for one or more aspects of the technology as described and illustrated herein, although some or all of the programmed instructions could be stored and/or executed elsewhere. A variety of different types of memory storage devices, such as a random access memory (RAM) or a read only memory (ROM) in the system or a floppy disk, hard disk, CD ROM, DVD ROM, or other computer readable medium which is read from and/or written to by a magnetic, optical, or other reading and/or writing system that is coupled to the processor 20, can be used for the memory 22. The interface unit 24 is used to operatively couple data communications between the viscosity computing device 16 and the viscosity measurement device 12 and differential amplifier 36, although other types and numbers of systems, devices, blades, components, and elements could be coupled together, such as one or more storage devices.

The viscosity computing device 16 receives the output signal from the differential amplifier 36 which can be displayed or otherwise processed to provide an output representative of the measured viscosity, such as the change in viscosity or the current viscosity of the measure media. By way of example only, the viscosity computing device 16 could compare the received output signal against other stored tables of output signals which previously have been correlated to viscosity measurements to determine a closest match and then output the corresponding viscosity measurement based on the closest match, although other manners for measuring or other processing the output signal could be used.

Although an exemplary environment the viscosity computing device 16 to receive the output signal is described and illustrated herein, other types and numbers of systems, devices, components, and elements in other configurations could be used for the viscosity computing device 16. It is to be understood that the systems of the examples described herein are for exemplary purposes, as many variations of the specific hardware and software used to implement the examples are possible, as will be appreciated by those skilled in the relevant art(s).

Furthermore, each of the processing systems of the examples may be conveniently implemented using one or more general purpose computer systems, microprocessors, digital signal processors, and micro-controllers, programmed according to the teachings of the examples, as described and illustrated herein, and as will be appreciated by those ordinary skill in the art.

In addition, two or more computing systems or devices can be substituted for any one of the systems in any example. Accordingly, principles and advantages of distributed processing, such as redundancy and replication also can be implemented, as desired, to increase the robustness and performance of the devices and systems of the examples. The examples may also be implemented on computer system or systems that extend across any suitable network using any suitable interface mechanisms and communications technologies, including by way of example only telecommunications in any suitable form (e.g., voice and modem), wireless communications media, wireless communications networks, cellular communications networks, G3 communications networks, Public Switched Telephone Network (PSTNs), Packet Data Networks (PDNs), the Internet, intranets, and combinations thereof.

The examples may also be embodied as a computer readable medium having instructions stored thereon for one or more aspects of the technology as described and illustrated by way of the examples herein, which when executed by a processor, cause the processor to carry out the steps necessary to implement the methods of the examples, as described and illustrated herein An exemplary operation of the viscometer system 10 to sense changes in viscosity of liquids or other fluids and determine viscosity will now be described with reference to FIGS. 1-3. The viscosity measurement device 12 is placed in a medium, such as a liquid or other fluid, whose viscosity is being measured.

Next, the driving device 14 is engaged so that the waveform generator 38 outputs an oscillating control signal, which is kept constant, to the gate of the NMOS field effect transistor 30, although other types oscillating non-oscillating control signals could be applied. This oscillating control signal turns the NMOS field effect transistor 30 on and off to control the application of voltage from the fifteen volt power source across the heating element 22 to generate heat, although other manners for generating heat and other power sources could be used. The resulting heating and cooling of the heating element 22 in response to the controlled application of voltage results in thermal expansion and contraction of membrane 20 along with metal plate 26. A large difference of thermal expansion coefficient between the plate 26 and the membrane 20 on the order of at least twenty helps to facilitate this thermal expansion and contraction.

In response to this displacement of the plate 26 and the membrane 20 during this repeated expansion and contraction, the resistances of each of the piezoresistive elements 28(1)-28(4) change. As described earlier, the piezoresistive elements 28(1)-28(4) are coupled as described earlier to form a piezoresistive Wheatstone bridge. One input 32 to an differential amplifier 36 is coupled between the piezoresistive elements 28(1) and 28(4) and another input 34 to the differential amplifier 32 is coupled between the piezoresistive elements 28(2) and 28(3) of this piezoresistive Wheatstone bridge, to provide an output signal to the viscosity computing device 16 representative of the measured displacement of the membrane 20, although the signal could be output to other types of devices. The viscosity computing device 16 receives this output signal which can be displayed or otherwise processed to provide an output representative of the measured viscosity of the media being analyzed, such as the change in viscosity or the current viscosity of the measure media. By way of example only, the viscosity computing device 16 could compare the received output signal against other stored tables of output signals which previously have been correlated to viscosity measurements to determine a closest match and then output the corresponding viscosity measurement based on the closest match, although other manners for measuring or other processing the output signal could be used.

In alternative example, the measurement of viscosity is the same as illustrated and described above, except as set forth below. In this example, the viscosity computing device 16 controls the driving device 14 to provide repeated high energy, short-duration heat pulses in the driving signal provided to the 30 heating element 22 membrane 20 with metal plate 26. The viscosity computing device 16 can determine an ideal duration for each of these pulses as explained in greater detail below. The rapidly heated heating element 22 resulting from these repeated high energy, short-duration heat pulses in the driving signal cause the membrane 20 with metal plate 26 to undergo a static deflection due to the heat expansion as well as dynamic deflection due to the inertial forces. The inertial forces generated in the rapidly heated heating element 22 lead the membrane 20 with metal plate 26 to resonate at its natural frequency. The displacement sensor apparatus 27 comprising the piezoresistive elements 28(1)-28(4) capture this resonating displacement and the viscosity computing device 16 receives the resulting output signal from the differential amplifier 36. The viscosity computing device 16 determines from the received output signal the natural resonant frequency and a quality factor of the fluid being measured which will vary based on the density and viscosity of the media being tested. From the determined resonant frequency and quality factor, the viscosity computing device 16 determines and provides a density and viscosity of the media being measured. By way of example only, the viscosity computing device 16 could compare the determined natural resonant frequency and Q factor against other stored tables of resonant frequency and Q factor which previously have been correlated to density and viscosity to determine a closest match and then output the corresponding density and viscosity based on the closest match, although other manners for measuring or other processing the output signal could be used.

The duration and magnitude of this heat pulse in the driving signal controlled by the deriving device 14 is not trivial, as thermal properties of the media, such as a liquid or other fluid, under test will affect the movement of the membrane 20 with metal plate 26 by driving the heat away. To avoid this, the heat pulse must to be short enough so that it is not influenced by the heat dissipation characteristics of the media, such as a liquid or other fluid. Pulse duration can be determined by the viscosity computing device 16 by calculating the time that it takes for a heat step input to travel through an insulating material. Using the one dimensional transient temperature equation—with K being the thermal diffusivity of the insulating material—for a semi-infinitely long body $x \geq 0$:

$$\frac{\partial T}{\partial t} = \kappa \frac{\partial^2 T}{\partial x^2} \qquad (1)$$

The solution with boundary conditions of T=Ta on x=0 and T=0 at t=0 is:

$$T = T_a \operatorname{erfc}\left(\frac{x}{2\sqrt{\kappa t}}\right) \qquad (2)$$

The natural frequency of vibration in vacuum of a simply supported square thin plate can be calculated using the following equation:

$$f_{vacuum} = \frac{19.74}{2\pi a^2}\left[\frac{Eh^3}{12\rho h(1-v^2)}\right]^{1/2} \qquad (3)$$

where E is the Young's modulus of the material, a is the length of plate, h its thickness, ρ its density and v its Poisson's ratio.

The frequency of vibration of a plate in a fluid will change according to the following equation. The result is depended on the density of the fluid $\rho_{fluid}$ and plate material $\rho_{plate}$, the radius of the circular plate a and its thickness h, as follow:

$$f_{fluid} = \frac{f_{vacuum}}{\sqrt{1+\beta}} \qquad (4)$$

where β

$$\beta = 0.669 \frac{\rho_{fluid} a}{\rho_{plate} h} \qquad (5)$$

The viscous effect on the natural frequency is found to be negligible for macroscopic plates, but when the thickness of the plate is reduced to the levels found of MEMS devices, such as membrane 20 with metal plate 26 it must be taken into account Taking the viscosity of the fluid into consideration as an energy dissipative element the added virtual mass factor is modified to be:

$$\beta = 0.6538 \frac{\rho_{fluid} a}{\rho_{plate} h}(1 + 1.082\xi) \qquad (6)$$

where the energy dissipation of the system is characterized by ξ, which is dependent on the kinematic viscosity υ, the radial frequency of vibration ω, and the radius a of the membrane 20 with metal plate 26. The Q factor, which is defined as the ratio between the energy stored and dissipated per cycle, becomes:

$$Q = 2\pi \frac{\text{energy\_stored}}{\text{energy\_dissipated\_per\_cycle}} \approx \frac{0.95}{\xi} \qquad (7)$$

and $$\xi = \sqrt{\frac{\upsilon}{\omega a^2}} \qquad (8)$$

Figure 4:
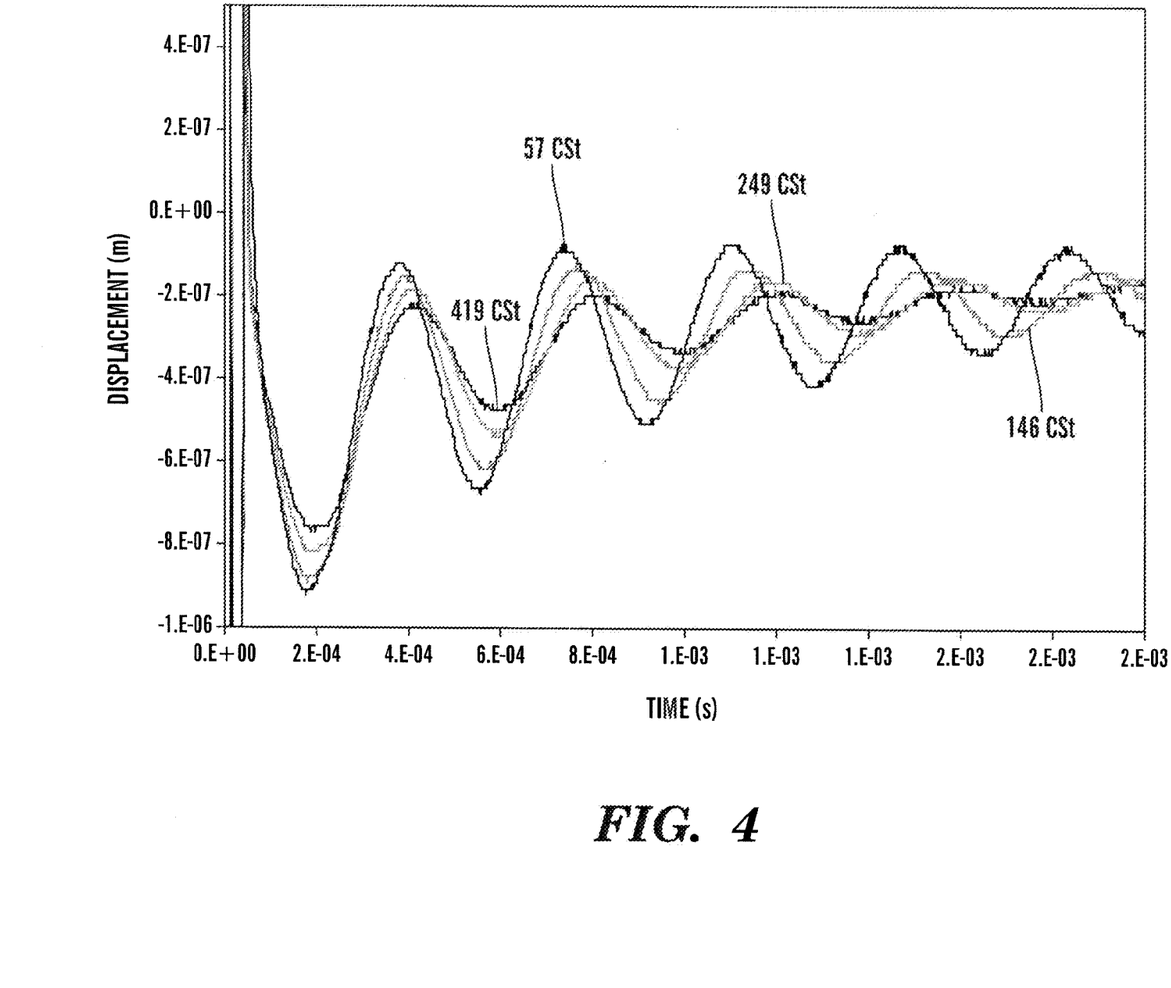
FIG. 4 is a graph of displacement of the exemplary viscosity measurement device when immersed in fluids of different viscosity values over time.
Figure 5:
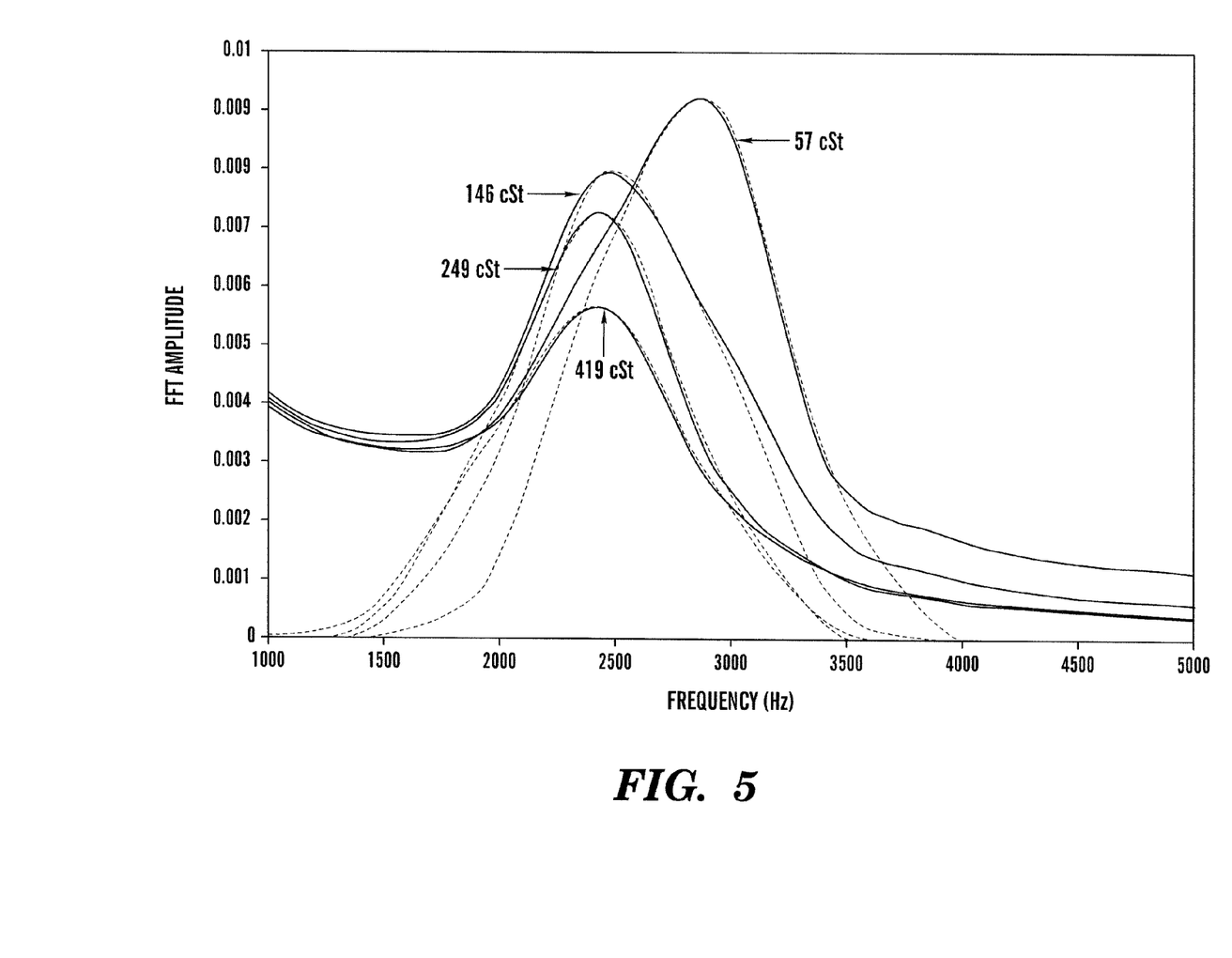
FIG. 5 is a graph of Fast Fourier Transform amplitude versus frequency for each of the fluids in which the exemplary viscosity measurement device was immersed in FIG. 4.

Therefore, knowing both the resonance frequency and the quality factor in the media, such as a liquid or other fluid, the viscosity computing device 16 can calculate the density and the viscosity of the media. The output from the viscosity measurement device 12 showing the displacement of the membrane 20 with metal plate 26 when immersed in media, such as a liquid or 15 other fluid, of different viscosity values over time is illustrated in FIG. 4. From these plots, values for the resonant frequency of vibration in each media can be extracted as well as a quality value Q, through the use of a Fast Fourier Transform technique as shown in FIG. 5. Resonant frequency and Q value can then be related by the viscosity computing device to viscosity and density of the media, 20 such as a liquid or other fluid, under test.

Accordingly, as illustrated and described with the examples herein, this technology can be used to inexpensively, reliably and in real time measure viscosity changes and/or determine viscosity and density of media, such as liquids or other fluids. This technology is compatible with current CMOS fabrication and provides an output signal for the viscosity reading that is compatible with current electronics and is easily integrated.

The theory and solutions relevant to thermal stress and actuation of a membrane 20 with a metal plate 26 as described and illustrated in the examples herein is set forth below. First order approximation equations are used to predict the general behavior of the bimetallic thermal actuated membranes. Experimental results are presented to understand the vertical movement with relation to the applied power. Additionally, the output response of the viscometer system 10 in fluid media with different viscosities is presented herein.

Analytical Approximation

The differential equation that models the interaction between the clamped thin square membrane 20 with the metal plate 26 actuated under a uniform step heat input over one face and a viscous fluid is:

$$D\nabla^4 w + \rho h \frac{\partial^2 w}{\partial t^2} = F_{fluid} - \frac{\nabla^2 M_T}{1-v}, \qquad (9)$$

where w is the vertical movement and $M_T$ is the thermal moment. D is the flexural rigidity, ρ the density and h the thickness of the plate. The function $F_{fluid}$ is the reaction force exerted by the surrounding medium on the plate. This function will not be solved here, but it has been shown to be significant enough to result in a dampening of the oscillation amplitude at low frequencies for high viscosity materials.

The solution to the vertical movement due to thermal stress of the membrane 20 with the metal plate 26 with fixed edges is complex and it usually requires the use of finite element analysis. As an initial approximation to understand the behavior of these structures was used. The vertical movement $y_c$ at the center of the membrane 20 with the metal plate 26 due to a temperature differential ΔT between the bottom and the top surfaces can be approximated by the following equation:

$$y_c = \frac{\gamma(1+v)\Delta T}{2t} r_o^2 \ln\frac{a}{r_o}, \qquad (10)$$

where γ is the temperature coefficient of expansion, υ is the Poisson's ratio of the material, t is the thickness of the plate, a is the radius of the membrane and $r_o$ is the radius of the heating element.

The same solution can be modified to determine the vertical movement of the membrane 20 with the metal plate 26 in which the thermal expansion coefficient of the two materials plays an important effect. The approximate solution is:

$$y_c = \frac{6(\alpha_b - \alpha_a)(T - T_0)(t_b + t_a)(1 + v_e)}{2 t_b^2 K_{1p}} r_o^2 \ln\frac{a}{r_o}, \quad (11)$$

where $$K_{1p} = 4 + 6\frac{t_a}{t_b} + 4\left(\frac{t_a}{t_b}\right)^2 + \frac{E_a t_a^3 (1 - v_b)}{E_b t_b^3 (1 - v_a)} + \frac{E_b t_b (1 - v_a)}{E_a t_a (1 - v_b)}, \quad (12)$$

and T is the temperature; $T_0$ is the temperature at which the diaphragm is flat; $\alpha_a$ and $\alpha_b$ are the thermal coefficient expansions of the materials (22 ppm/° C. for aluminum and 2.33 ppm/° C. for silicon), $t_a$ and $t_b$ are the thickness; $v_e$ the effective Poisson's ratio of the composite membrane ($v_e \sim v_a \sim v_b \sim 0.3$); $r_o$ in this case is taken as the radius of the bimetal area; a is the membrane radius.

The solution presented above requires that the membrane 20 with the metal plate 26 be able to expand and contract in its plane at the edges of the membrane 20, which is not the case in these examples where the edges of the membrane 20 are fixed to the stationary bulk silicon supporting structure 18 and develop in-plane resisting forces. It also does not take into account the 1 μm $SiO_2$ thermal isolation layer 24 that is used to maintain the heating element 22 contained to the silicon membrane 20. Nevertheless these equations can be used for a first order approximation of the behavior of thermally actuated bimetallic membranes, such as the membrane 20 with the metal plate 26.

Figure 10A:
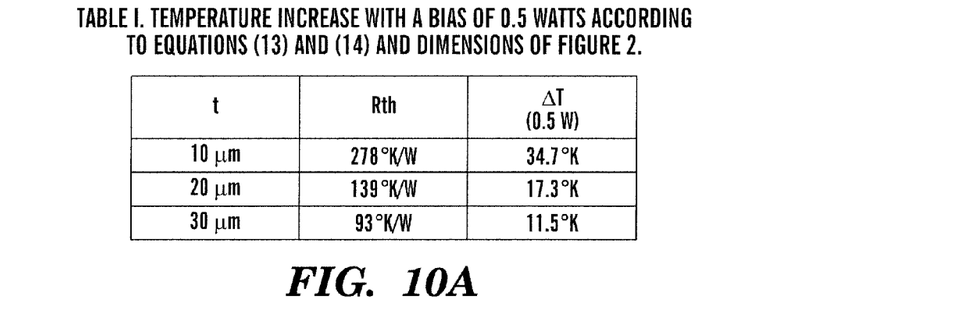
FIG. 10A is a table of expected temperature increase with a bias of 0/5 watts.

A factor to be able to use these approximations is to have a good understanding of the heating mechanism of the membrane 20. For the presented actuator a p-type diffused resistor is used as the heating element 22. A first order approximation to the Joule heating obtained with the P+ silicon heater can be obtained by calculating the thermal resistance of the silicon membrane 20 with the dimensions presented in FIG. 2. To simplify the analysis of this structure, the temperature is assumed to be maximum and uniform across the volume of the heating element 22. It is also assumed to be uniform across the z-axis and to decrease linearly from the edge of the heating element 22 to the bulk silicon membrane 20, which is assumed to be an ideal heat sink at room temperature. Equations (13) and (14) are used to predict the temperature of the membrane 20. The thermal conductivity of silicon $C_{Si}=1.5$ W/cm° K was used, since the main component of the diaphragm is silicon. The length to ambient is the distance from the edge of the heating resistor to the bulk silicon, L=500 μm an and A varies with the cross-sectional area of the silicon membrane. For this approximation the resistance dependence on temperature of the P+ diffused resistive heating element 22r was not taken into account. The predicted temperature is calculated for 50 mA of current through the 200Ω resistor. Table I illustrated in FIG. 10A shows the expected temperature increase under these bias conditions for silicon membranes 20 of different thickness. These temperature values are used to compute the expected vertical movement at the center of the membrane 20 with varying bimetallic areas. The results are presented in Table II shown in FIG. 10B.

$$R_{thermal} = \frac{1}{C_{Si}} \frac{L}{A} \quad (13)$$

$$T = T_o + I^2 R\left(\frac{R_{thermal}}{4}\right) \quad (14)$$

Fabrication

In this example, a bulk MEMS microfabrication process was used to fabricate the viscosity measurement device 12. The fabrication process starts with a bare double-side-polished n-type silicon wafer to form the membrane 20 and supporting structure or substrate 18. A silicon oxide is grown and used as a masking layer for the P+ spin-on-dopant process, which acts as the heating element 22 spaced in from the edges of the membrane 20. After this, a pad silicon oxide is thermally grown and silicon nitride is deposited using a low-pressure chemical vapor deposition (LPCVD) process. The silicon nitride is used as a protection layer during the KOH etch. Before continuing with the KOH etching, the wafer is processed through the backside photolithography step. The patterned silicon nitride and oxide are then removed from the backside of the wafers by dry $SF_6$ and HF etch respectively. Diaphragm thicknesses in the range of 10 to 40 μm have been achieved with this process. After the silicon membrane 18 with the heating element 26 is created, both the protective silicon nitride and the remaining pad silicon oxide are removed. Polysilicon is then deposited via LPCVD on top of an insulating oxide layer 24 and doped.

The Wheatstone Piezoresistive bridge, comprising the displacement sensor apparatus 27 with the piezoresistive elements 28(1)-28(4), utilizes n-type doped polysilicon. A low temperature oxide layer is then deposited and contact openings to the heating element 22 and the piezoresistive elements 28(1)-28(4) are etched out in an HF solution. After the contacts are etched, a metal layer of 10,000 Å of aluminum is deposited and then patterned to make the electrical connections to the ends of each of the heating element 22 and the piezoresistive elements 28(1)-28(4) and to form the metal plate 26 of the viscosity measurement device 12.

Experimental Results

Three exemplary viscosity measurement devices 12 comprising Si/Al bimetal structures were fabricated with bimetallic areas comprising membrane 20 and metal plate 26 of 0% (i.e. no metal plate 26 in this example), 5% and 25% in order to study the effects of the bimetal area on vertical movement. The percentage refers to the percent area of the membrane 20 that is covered by the metal plate 26 and thus being of bimetal composition. The piezoresistive elements 28(1)-28(4) form the Wheatstone bridge that is used to monitor the strain at the edges of the square diaphragms, comprising membrane 20 in the 0% example and membrane 20 with metal plate 26 in the 5% and 25% examples, which is proportional to the displacement of the membrane 20 or membrane 20 with metal plate 26. This displacement was measured in these examples with a real-time dynamic optical surface profiler. The displacement is first calibrated to the voltage output of the Wheatstone bridge by stepping the power through the resistive heating element 22 and measuring the displacement after a settling time. A good fit is obtained for a linear relationship of 3.696 μm/mV/V with and Rsq value of 0.9. This sensitivity correlation enables measurement of displacement of different exemplary viscosity measurement devices 12 without the need of complex and expensive optical measuring tools.

Figure 6:
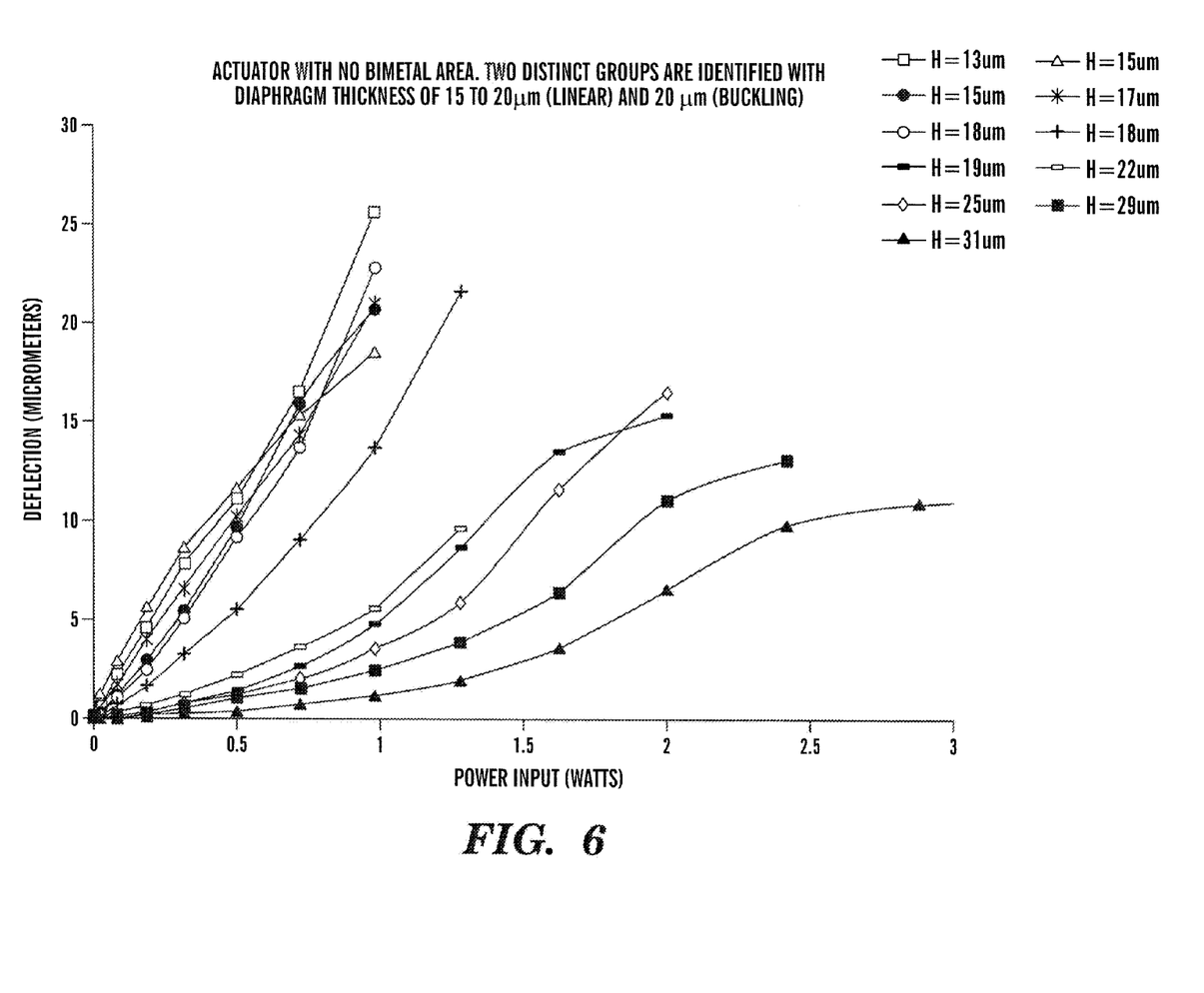
FIG. 6 is a graph of experimental results with a viscosity measurement device with no bimetal area.

Referring to FIG. 6, the measured results of the exemplary viscosity measurement devices 12 with no metal plate 26 (i.e. 0%) are illustrated. The displacement or deflection is measured as the power is increased through the heating element 22 for the exemplary viscosity measurement devices 12 with different thickness for membrane 20. The response of the exemplary viscosity measurement devices 12 is linear with power for devices with membrane thicknesses of about 15-20 µm at a rate of 20.8 µm/W. As the thickness of the membrane 20 increases above 20 µm the deflection is significantly lower and it remains linear up to about 1 Watt at which point it increases abruptly before leveling at 2 Watts. This non-linear relation between vertical movement and temperature can be explained by the increase in axial load at higher temperatures, which leads to the buckling of the structures.

Figure 7:
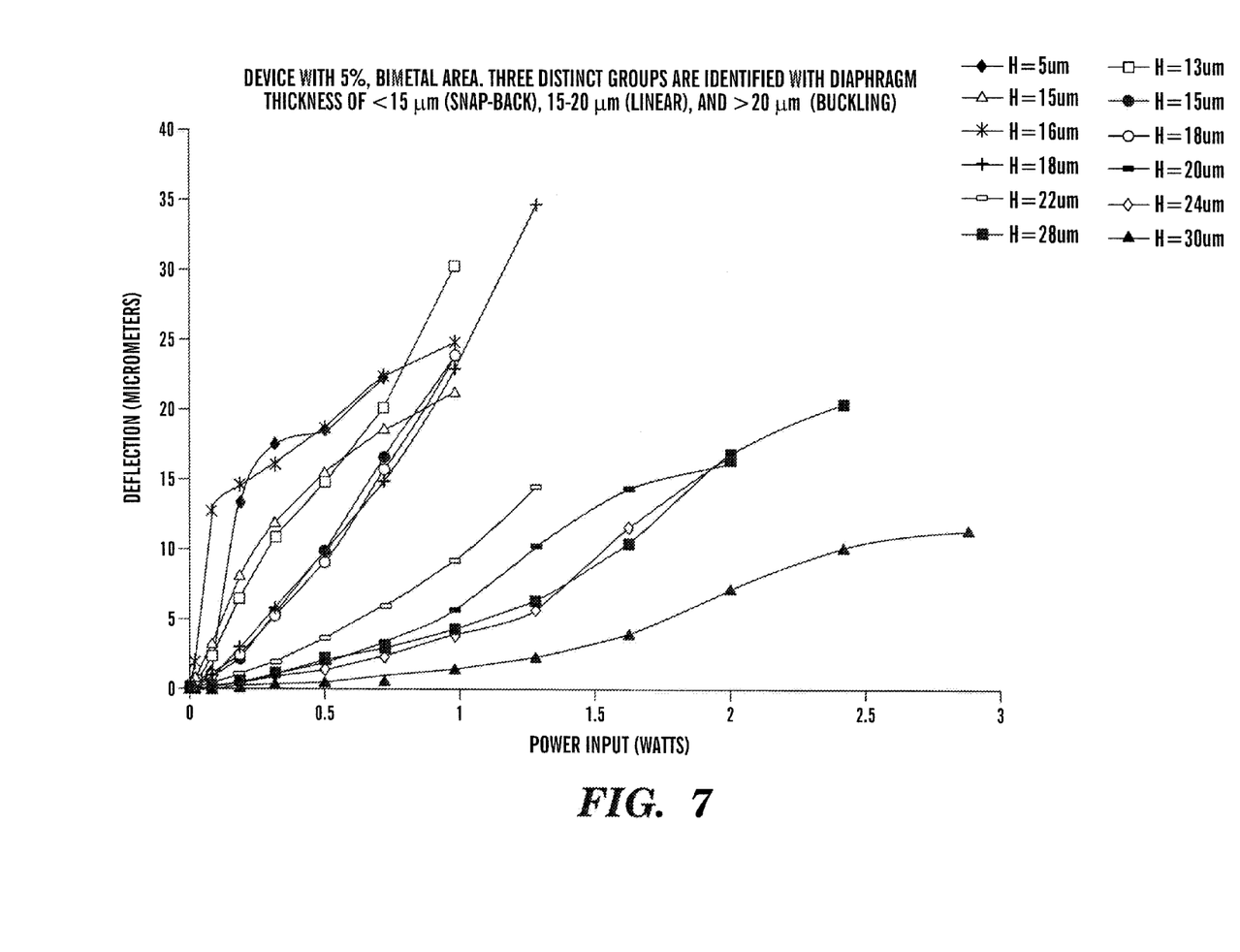
FIG. 7 is a graph of experimental results with a viscosity measurement device with a 5% bimetal area.

Referring to FIG. 7, the results of exemplary viscosity measurement devices 12 with a 5% bimetal composition of metal plate 26 on membrane 20 are illustrated. It can be observed that for exemplary viscosity measurement devices 12 with thinner membranes 20 of 5 µm to 15 µm, there seems to be a rapid increase in deflection at low power levels leading to structural buckling. This buckling was observed to be a snapping effect, which is characteristic of bimetal structures and has to do with the different equilibrium shapes that develop when the transverse loading is increased as an effect of the temperature. When the temperature is increased the first snapping action occurs, when the temperature is reduced the snap-back action takes place. This effect is efficiently used in thermostats and in some MEMS applications to sense temperature changes. The exemplary viscosity measurement devices 12 with membrane 20 thickness between 15 µm and 20 µm show a linear relation to power at a rate of 25.5 µm/W. As the membrane thickness increases, the exemplary viscosity measurement devices 12 shows a similar behavior to the previous exemplary viscosity measurement devices 12, seemingly buckling at about 1.25 W before saturating at about 2 W. A snap-back effect is not observed for these exemplary viscosity measurement devices 12 with thicker membranes 20.

Figure 10B:
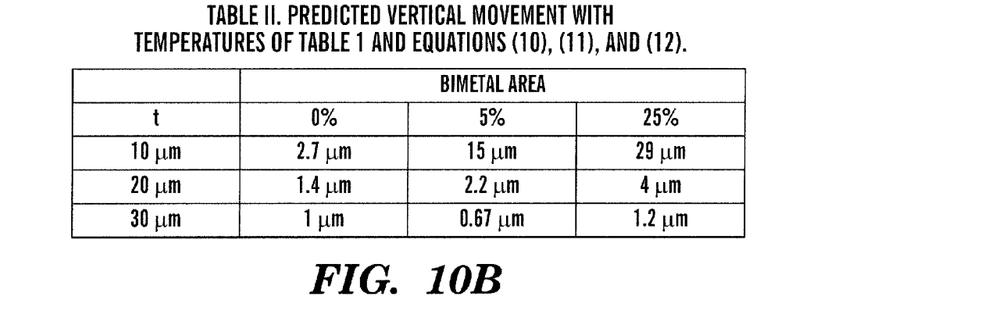
FIG. 10B is a table of predicted deflection movement.
Figure 10C:
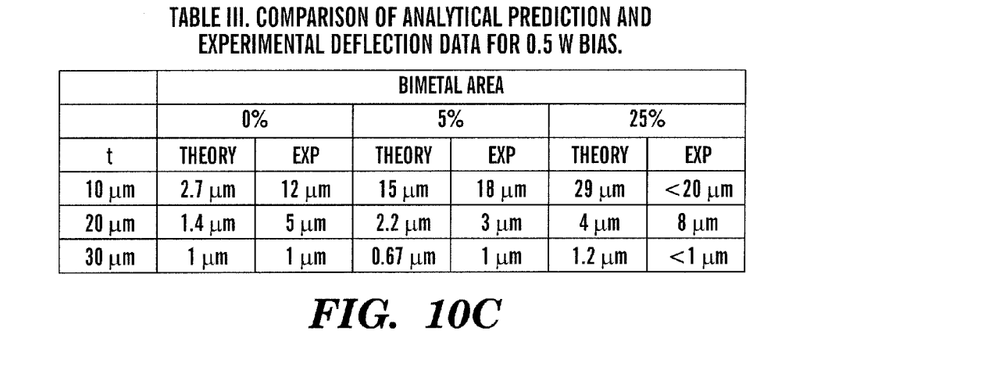
FIG. 10C is a table of predicted deflection movement against experimental deflection movement data.

The values obtained during experimental testing match those predicted analytically in Table II shown in FIG. 10B, with the exception of the devices with 0% of bimetal area. Table III shown in FIG. 10C presents the comparison of deflection data for a 0.5-Watt bias. The mismatch of the exemplary viscosity measurement devices 12 with no bimetal area is due to the fact that the theoretical solutions presented above do not take into account the in-plane resisting forces that develop against the bulk silicon supporting structure or substrate 18 and thus underestimate the vertical deflection of these structures. On the other hand, the fact that the experimental results match the analytical prediction of the exemplary viscosity measurement devices 12 with 5% and 25% indicate that the bimetal effect overtakes the effect of the axial forces against the bulk silicon supporting structure 18. As such, the preceding equations offer good approximations to the actual results when bimetal structures are used.

Figure 8:
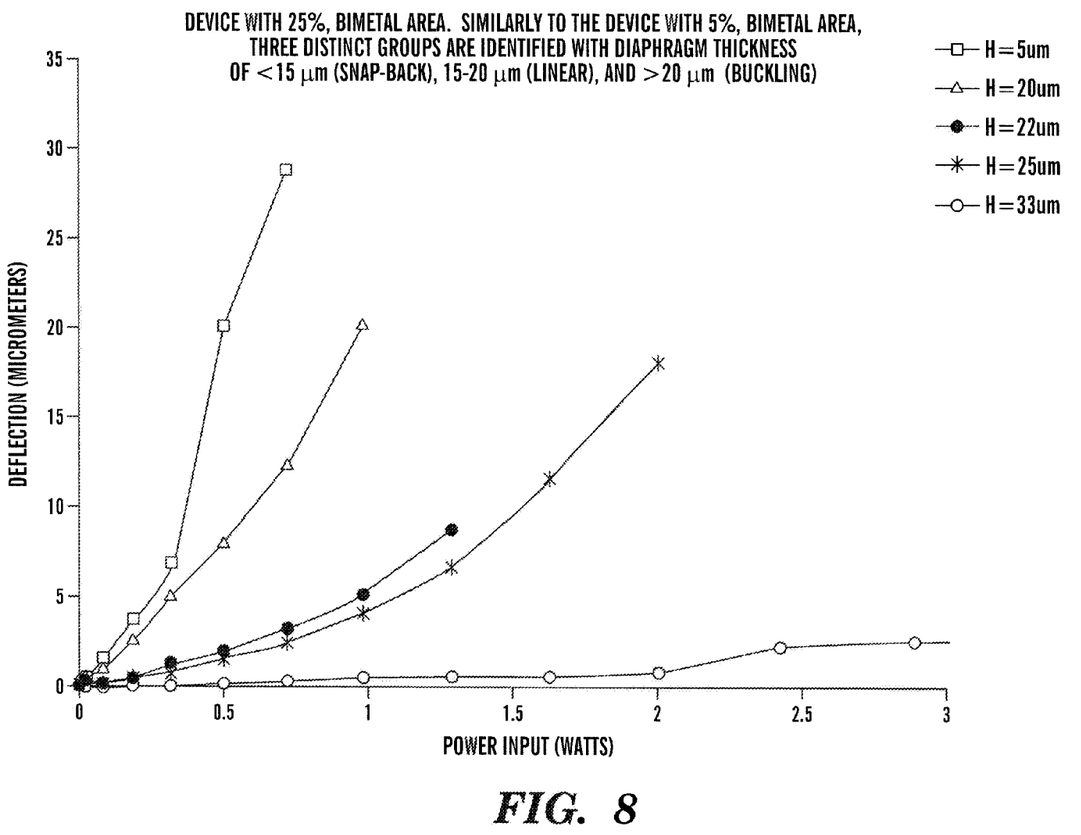
FIG. 8 is a graph of experimental results with a viscosity measurement device with a 25% bimetal area.

Referring to FIG. 8, the results of exemplary viscosity measurement devices 12 with a 25% bimetal composition of metal plate 26 on membrane 20 are illustrated. Even though the amount of data is limited, the same observations can be made as the device with 5% bimetal area. For exemplary viscosity measurement devices 12 with thinner membranes 20 the snap-back effect is observed. Only one exemplary viscosity measurement devices 12 with the medium range of membrane thickness was available for testing, but the resulting linear relation of deflection and power is in the same range as that of the 5% bimetal area devices. For exemplary viscosity measurement devices 12 with thicker membranes 20 a buckling effect is again observed at about 1.25 W with no snap-back.

In order to choose a reliable viscosity measurement device 12 to be operated at a frequency range of 10-20 Hz it is suggested to stay away from any temperature ranges that would lead to instabilities in the structures, such as buckling or snap-back. Thus, exemplary viscosity measurement devices 12 with a thickness range of 15 to 20 µm for membrane 20 are chosen in these examples. The bias of operation is kept relatively low at 0.5 Watts. According to the calculations presented above, this corresponds to a temperature increase of only 15° C. to 30° C. At this temperature range buckling of the membrane 20 is not expected, thus preventing material fatigue and premature failure.

An exemplary viscosity measurement device 12 with a 5% metal plate area and a membrane thickness of 15 µm was chosen to test the feasibility of utilizing these viscosity measurement devices 12. The linear relationship with temperature of this viscosity measurement device 12 allows us to accurately control the amplitude of oscillation.

Figure 9:
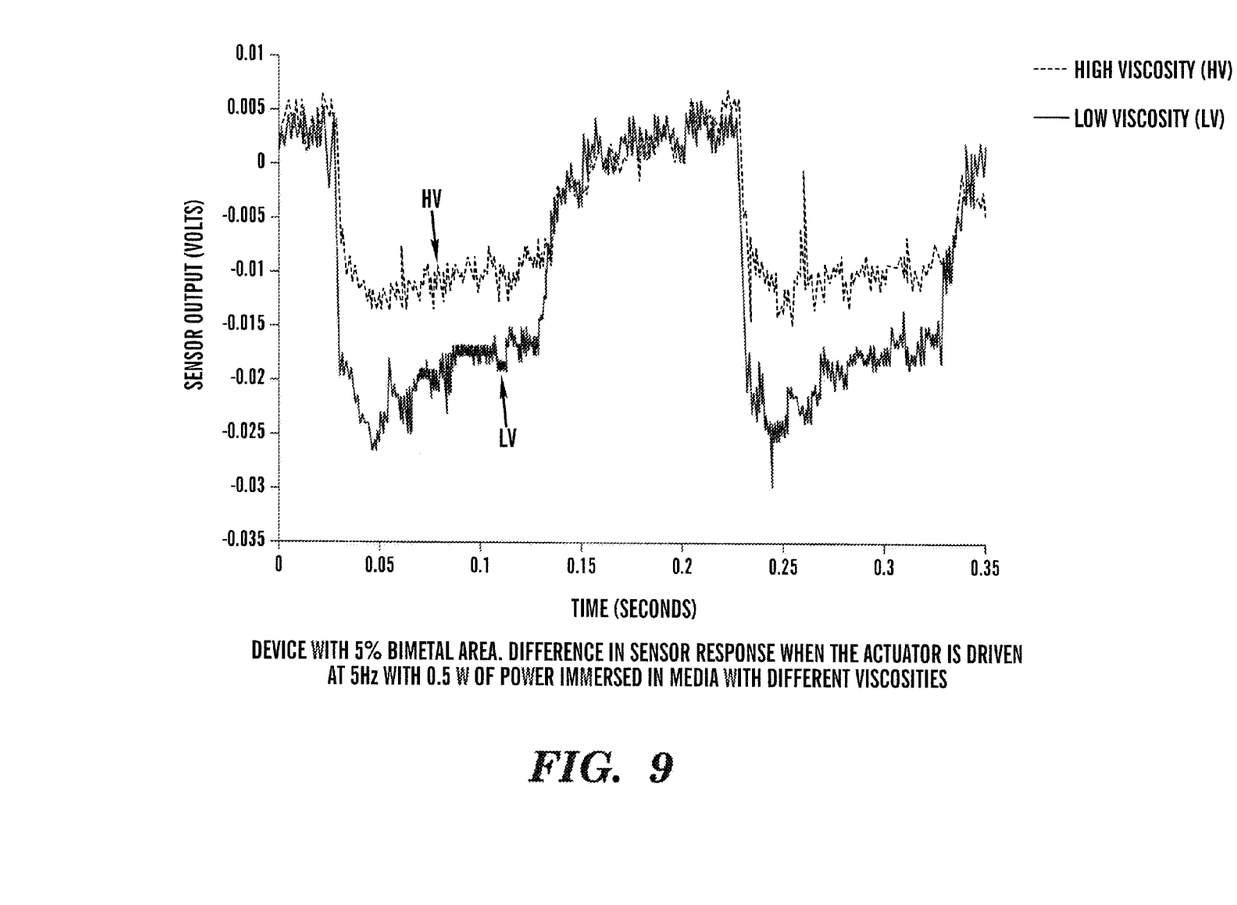
FIG. 9 is a graph of the output voltage signal from a piezoresistive Wheatstone bridge biased with 5 V when an exemplary viscosity measurement device is operated in air and in a medium of higher viscosity.

Referring to FIG. 9, a graph of the output voltage of the piezoresistive Wheatstone bridge biased with 5 V when this exemplary viscosity measurement device 12 as described herein is operated in air (i.e. low viscosity (LV) medium) and in a medium of higher viscosity (i.e. high viscosity (HV) medium) is illustrated. The actual viscosity value of this media is not known, but it is significantly higher than air. The thermal heating element 22 is driven by the driving system 14 with a square wave of 50 mA at a frequency of 5 Hz and 50% duty cycle from the waveform generator 38. In this particular viscosity measurement device 12, due to non-ideal asymmetry of the Wheatstone bridge resistors 28(1)-28(4), the membrane 20 is actually deflected up when the voltage output goes negative. As such, the maximum output voltage difference is about 12 mV, which correspond to a vertical displacement or deflection difference of 8.8 µm and takes place when the membrane 20 first pushes up against the medium being measured. This is a significance difference and confirms the feasibility of this technology. It is also important to note that the amplitude difference depends on the frequency of actuation. Data has shown that the amplitude difference can be at a maximum between 5 and 10 Hz for this particular example.

Accordingly, a proof of concept of a MEMS based viscometer system 10 is illustrated and described herein. The viscosity measurement device 12 is based on a membrane 20, heating element 22, metal plate 26 and piezoresistive elements 28(1)-28(4) which are CMOS compatible. The exemplary study of the thermal actuation of the thin silicon membrane 20 herein has shown that a bimetal area 5% is sufficient to achieve a significant vertical deflection for a power bias of 0.5 Watts, which corresponds to a temperature increase between 15° C. and 30° C. Additionally, exemplary results have been presented herein with reference to FIG. 9 which show the oscillation amplitude of the membrane 20 with the metal plate 26 changes when the exemplary viscosity measurement device 12 is immersed in media of different viscosity.

Having thus described the basic concept of the invention, it will be rather apparent to those skilled in the art that the foregoing detailed disclosure is intended to be presented by way of example only, and is not limiting. Various alterations, improvements, and modifications will occur and are intended to those skilled in the art, though not expressly stated herein. These alterations, improvements, and modifications are intended to be suggested hereby, and are within the spirit and scope of the invention. Additionally, the recited order of processing elements or sequences, or the use of numbers, letters, or other designations therefore, is not intended to limit the claimed processes to any order except as may be specified in the claims. Accordingly, the invention is limited only by the following claims and equivalents thereto.

What is claimed is:

1. A viscometer system comprising:
   a viscosity measurement device comprising:
   a flexible membrane;
   a supporting structure which supports and fixes an entire outer periphery of a moveable portion of the flexible membrane;
   an actuation heating element on and spaced in from the outer periphery of the flexible membrane which provides the heat to create thermal expansion differences between the membrane and a metal plate which is in at least partial alignment with the actuation heating element; and
   at least one displacement sensor coupled to the flexible membrane that measures the displacement of the membrane with the metal plate and outputs a displacement signal representative of a viscosity of a fluid in contact with the flexible membrane.

2. The system as set forth in claim 1 further comprising a driving device configured to apply a driving signal at a first frequency and substantially constant power to the actuation heating element.

3. The system as set forth in claim 2 further comprising a viscosity computing device configured to determine and provide a viscosity of the fluid in contact with the flexible membrane based on the displacement signal.

4. The system as set forth in claim 3 wherein the viscosity computing device is further configured to determine from the displacement signal a resonant frequency or a quality factor in the fluid and determines and provides at least one of density or the viscosity of the fluid based on the determined resonance frequency and the quality factor.

5. The system as set forth in claim 4 wherein the viscosity computing device is further configured to determine a first duration for a pulse of the driving signal which is uninfluenced by the heat dissipation characteristics of the fluid and controls the driving device to apply the driving signal with the determined pulse.

6. The system as set forth in claim 1 wherein the at least one displacement sensor comprises a plurality of piezoresistive sensing elements on the flexible membrane.

7. The system as set forth in claim 6 wherein the plurality of piezoresistive sensing elements further comprise a piezoresistive Wheatstone bridge.

8. The system as set forth in claim 6 wherein the flexible membrane further comprises a silicon substrate, the actuation heating element further comprises a doped region in the silicon substrate, and the plurality of piezoresistive sensing elements further comprise doped polysilicon.

9. The system as set forth in claim 1 further comprising a thermal isolation layer formed over the actuation heating element and the flexible membrane.

10. The system as set forth in claim 1 further comprising a thermal isolation layer disposed between the actuation heating element and the metal plate.

11. A method of making a viscosity measurement device, the method comprising:
    providing an actuation heating element on and spaced in from an outer periphery of a flexible membrane which provides the heat to create thermal expansion differences between the membrane and a metal plate which is in at least partial alignment with the actuation heating element, the entire outer periphery of a moveable portion of the flexible membrane supported and fixed by a supporting structure;
    coupling at least one displacement sensor to the flexible membrane that measures the displacement of the membrane with the metal plate and outputs a displacement signal representative of a viscosity of a fluid in contact with the flexible membrane.

12. The method as set forth in claim 11 further comprising a providing a driving device configured to apply a driving signal at a first frequency and substantially constant power to the actuation heating element.

13. The method as set forth in claim 12 further comprising providing a viscosity computing device configured to determine and output a viscosity of the fluid in contact with the flexible membrane based on the displacement signal.

14. The method as set forth in claim 13 wherein the providing a viscosity computing device further comprises providing a viscosity computing device further configured to determine from the displacement signal a resonant frequency and a quality factor in the fluid and determine and provide at least one of density or the viscosity of the fluid based on the determined resonance frequency and the quality factor.

15. The method as set forth in claim 14 wherein the providing a viscosity computing device further comprises providing a viscosity computing device further configured to determine a first duration for a pulse of the driving signal which is uninfluenced by the heat dissipation characteristics of the fluid and controls the driving device to apply the driving signal with the determined pulse.

16. The method as set forth in claim 11 wherein the coupling at least one displacement sensor comprises forming a plurality of piezoresistive sensing elements on the flexible membrane.

17. The method as set forth in claim 16 wherein the forming the plurality of piezoresistive sensing elements further comprise forming a piezoresistive Wheatstone bridge on the flexible membrane.

18. The method as set forth in claim 16 wherein the flexible membrane further comprises a silicon substrate, the actuation heating element further comprises a doped region in the silicon substrate, and the plurality of piezoresistive sensing elements further comprise doped polysilicon.

19. The method as set forth in claim 11 further comprising providing a thermal isolation layer formed over the actuation heating element and the flexible membrane.

20. The method as set forth in claim 11 further comprising providing a thermal isolation layer disposed between the actuation heating element and the metal plate.

21. A viscometer system comprising:
    a flexible membrane;
    an actuation heating element on and spaced in from an outer periphery of the flexible membrane which provides the heat to create thermal expansion differences between the membrane and a metal plate which is in at least partial alignment with the actuation heating element;
    a driving device configured to apply a driving signal at a first frequency and substantially constant power to the actuation heating element;
    at least one displacement sensor coupled to the flexible membrane that measures the displacement of the membrane with the metal plate and outputs a displacement signal representative of a viscosity of a fluid in contact with the flexible membrane; and
    a viscosity computing device configured to determine and provide a viscosity of the fluid in contact with the flexible membrane based on the displacement signal, to determine from the displacement signal a resonant frequency and a quality factor in the fluid and determines and provides at least one of density or the viscosity of the fluid based on the determined resonance frequency and the quality factor, and to determine a first duration for a pulse of the driving signal which is uninfluenced by the heat dissipation characteristics of the fluid and controls the driving device to apply the driving signal with the determined pulse.

22. The system as set forth in claim 21 further comprising a thermal isolation layer formed over the actuation heating element and the flexible membrane.

23. The system as set forth in claim 21 further comprising a thermal isolation layer disposed between the actuation heating element and the metal plate.

24. A method of making a viscosity measurement device, the method comprising:
   providing an actuation heating element on and spaced in from an outer periphery of a flexible membrane;
   providing at least one metal plate on the flexible membrane and at least in partial alignment with the actuation heating element;
   providing a driving device configured to apply a driving signal at a first frequency and substantially constant power to the actuation heating element;
   coupling at least one displacement sensor to the flexible membrane that measures the displacement of the membrane with the metal plate and outputs a displacement signal representative of a viscosity of a fluid in contact with the flexible membrane;
   providing a viscosity computing device configured to determine and output a viscosity of the fluid in contact with the flexible membrane based on the displacement signal, to determine from the displacement signal a resonant frequency and a quality factor in the fluid and determine and provide at least one of density or the viscosity of the fluid based on the determined resonance frequency and the quality factor, and to determine a first duration for a pulse of the driving signal which is uninfluenced by the heat dissipation characteristics of the fluid and controls the driving device to apply the driving signal with the determined pulse.

25. The method as set forth in claim 24 further comprising providing a thermal isolation layer formed over the actuation heating element and the flexible membrane.

26. The method as set forth in claim 24 further comprising providing a thermal isolation layer disposed between the actuation heating element and the metal plate.

27. A viscometer system comprising:
   a flexible membrane;
   a supporting structure which supports and fixes an entire outer periphery of the flexible membrane;
   an actuation heating element on and spaced in from an outer periphery of the flexible membrane which provides the heat to create thermal expansion differences between the membrane and a metal plate which is in at least partial alignment with the actuation heating element;
   a driving device configured to apply a driving signal at a first frequency and substantially constant power to the actuation heating element;
   at least one displacement sensor coupled to the flexible membrane that measures the displacement of the membrane with the metal plate and outputs a displacement signal representative of a viscosity of a fluid in contact with the flexible membrane; and
   a viscosity computing device configured to determine and provide a viscosity of the fluid in contact with the flexible membrane based on the displacement signal,
   wherein the viscosity computing device is further configured to determine from the displacement signal a resonant frequency or a quality factor in the fluid and determines and provides at least one of density or the viscosity of the fluid based on the determined resonance frequency and the quality factor, and
   wherein the viscosity computing device is further configured to determine a first duration for a pulse of the driving signal which is uninfluenced by the heat dissipation characteristics of the fluid and controls the driving device to apply the driving signal with the determined pulse.

28. The system as set forth in claim 27 further comprising a thermal isolation layer formed over the actuation heating element and the flexible membrane.

29. The system as set forth in claim 27 further comprising a thermal isolation layer disposed between the actuation heating element and the one metal plate.

30. A method of making a viscosity measurement device, the method comprising:
   providing an actuation heating element on and spaced in from an outer periphery of a flexible membrane, an entire outer periphery of the flexible membrane supported and fixed by a supporting structure;
   providing at least one metal plate on the flexible membrane and at least in partial alignment with the actuation heating element;
   providing a driving device configured to apply a driving signal at a first frequency and substantially constant power to the actuation heating element;
   coupling at least one displacement sensor to the flexible membrane that measures the displacement of the membrane with the metal plate and outputs a displacement signal representative of a viscosity of a fluid in contact with the flexible membrane; and
   providing a viscosity computing device configured to determine and output a viscosity of the fluid in contact with the flexible membrane based on the displacement signal,
   wherein the providing a viscosity computing device further comprises providing a viscosity computing device further configured to determine from the displacement signal a resonant frequency and a quality factor in the fluid and determine and provide at least one of density or the viscosity of the fluid based on the determined resonance frequency and the quality factor, and
   wherein the providing a viscosity computing device further comprises providing a viscosity computing device further configured to determine a first duration for a pulse of the driving signal which is uninfluenced by the heat dissipation characteristics of the fluid and controls the driving device to apply the driving signal with the determined pulse.

31. The method as set forth in claim 30 further comprising providing a thermal isolation layer formed over the actuation heating element and the flexible membrane.

32. The method as set forth in claim 30 further comprising providing a thermal isolation layer disposed between the actuation heating element and the metal plate.

* * * * *